United States Patent

Salamon et al.

[11] Patent Number: 5,166,354
[45] Date of Patent: Nov. 24, 1992

[54] QUINOLINE DERIVATIVES AND PROCESSES FOR THE PREPARATION THEREOF

[75] Inventors: Zoltán Salamon, Debrecen; József Jekö; Ilona Imre, both of Tiszavasvári; Magdolna Czellér, Hajdunánás, all of Hungary

[73] Assignee: Alkaloida Vegyeszeti Gyar, Tiszavasvari, Hungary

[21] Appl. No.: 671,916

[22] PCT Filed: Jul. 20, 1990

[86] PCT No.: PCT/HU90/00050
§ 371 Date: Mar. 19, 1991
§ 102(e) Date: Mar. 19, 1991

[87] PCT Pub. No.: WO91/01315
PCT Pub. Date: Feb. 7, 1991

[30] Foreign Application Priority Data

Jul. 25, 1989 [HU] Hungary ............................. 3736/89

[51] Int. Cl.$^5$ .......................................... C07D 403/06
[52] U.S. Cl. ..................................... 546/176; 546/152; 546/167
[58] Field of Search ........................................ 546/176

[56] References Cited

FOREIGN PATENT DOCUMENTS

WO91/01315 2/1991 PCT Int'l Appl. .

Primary Examiner—David B. Springer
Attorney, Agent, or Firm—Herbert Dubno; Jonathan Myers

[57] ABSTRACT

The invention relates to a processes for the preparation of quinoline derivatives of the general formula (I)

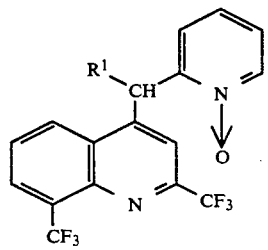

wherein
R$^1$ stands for hydrogen or a group of the formula (II)

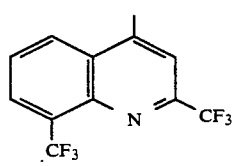

which are intermediates for pharmaceutically active compounds.

6 Claims, No Drawings

QUINOLINE DERIVATIVES AND PROCESSES FOR THE PREPARATION THEREOF

CROSS REFERENCE TO RELATED APPLICATION

This application is a national phase of PCT/HU90/00050 filed Jul. 20, 1990 and based upon Hungarian national application A3736/89 filed Jul. 25, 1989 and modified Jul. 3, 1990, under the International Convention.

FIELD OF THE INVENTION

The present invention is directed to a process for the preparation of quinoline derivatives of the formula (I)

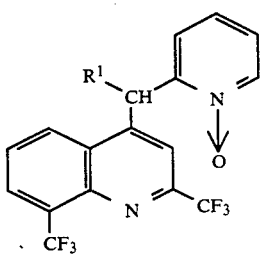

(I)

wherein
R¹ stands for hydrogen or a group of the formula (II)

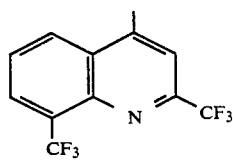

(II)

by reacting a halogen quinoline derivative of the formula (III)

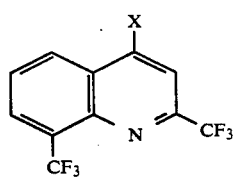

(III)

wherein
X stands for chlorine or bromine with picoline oxide of the formula (IV)

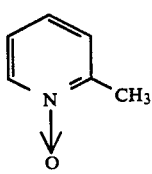

(IV)

in the presence of alkali-t-alkylate, preferably potassium-t-butylate or
b) oxidizing a compound of the formula (V).

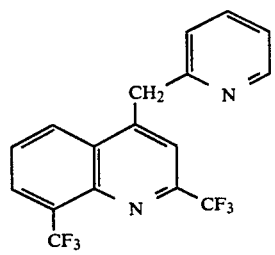

(V)

The definition of the substituents is as follows:
R¹ stands for hydrogen or a group of the formula (II)
X stands for chlorine or bromine.

The novel compounds according to the present invention are important intermediates for the preparation of pharmaceutically active compounds. Thus, for instance the novel compounds are valuable intermediates of erythro-alpha-2-piperidyl-2,8-bis(trifluoro-methyl)-quinoline-4-methanol-hydrochloride (meflokin) or mefloquin. This latter active ingredient can be successfully used in pharmaceutically active compositions against malaria.

BACKGROUND OF THE INVENTION

Meflokin has been first prepared (see J. Med. Chem. 14, 926 (1971)) by reacting a 2,8-bis(trifluoro-methyl)-quinoline-4-carboxylic acid synthesized in three steps with 2-lithio-pyridine and by hydrating the obtained 2-pyridyl-2,8-bis(trifluor-methyl)-quinolyl-ketone ("Ketone") above Adams-catalyst. From the above quinoline carboxylic acid intermediate the ketone was obtained also by reacting it with 2-bromo-magnesium-pyridine (DOS 29 40443), and by hydrogenating the "ketone" analogously to meflokin above a platina charcoal catalyst. The unisolated intermediate of the reduction step (2-pyridyl)-2,8-bis(trifluor-methyl)-quinoline-4-methanol is referred to hereinafter as "Oxy-methane". This compound can be obtained also by reacting 4-lithio-quinoline derivatives obtained from 2,8-bis(trifluoro-methyl)-4-bromo-quinoline by lithiation with 2-pyridine-aldehyde (DOS 28066909). According to a newer technical solution the metallation step is eliminated and thereby a less expensive starting material can be used compared to the so far known quinoline intermediates. When reacting 2,8-bis(trifluoro-methyl)-4-chloro-quinoline with 2-pyridyl-acetonitrile or with 2-pyridyl-methyl-phosphonium salt the obtained intermediate results in ketone by oxidation. According to the authors in these cases in order to subject the halogen of the quinoline in 4-position to nucleophilic substitution the pyridine reactant has to contain on the methyl group an electron withdrawing substituent (see the above mentioned carbonitrile or phosphonium group) (EP0049776).

In EPA 0049 776 in Example 1 the aromatic nucleophilic substitution of 2-methyl-pyridine-N-oxide has been mentioned and was carried out with sodium amide in dimethoxy-ethane, but the structure of the obtained product has not been determined, no physical-chemical data were given and the reference was cancelled from the granted patent.

The above mentioned processes have several disadvantages, such as the already mentioned metallation steps or the expensive quinoline intermediates (such as 2,8-bis(trifluoro-methyl)-4-bromo-quinoline or the corresponding quinoline-4-carboxylic acid) and the pyridine derivatives are expensive and not easily accessible.

These disadvantages could be successfully eliminated by using a quinoline intermediate of the formula (III) and 2-methyl-pyridine-N-oxide. The quinoline intermediate of the formula (III) is prepared by our method disclosed in U.S. Pat. No. 4,599,345 and U.S. Pat. No. 4,659,834 which is also suitable for the industrial synthesis of 2,8-bis(trifluoro-methyl)-4-chloro-quinoline. We have now found that as opposed to the teaching of EP 0 049 776 the electron withdrawing substituent is not necessary on the methyl group of picoline as the cheaper and more easily accessible 2-methyl-pyridine-N-oxide can be reacted without the electron withdrawing substituent as well.

DESCRIPTION OF THE INVENTION

According to the present invention di(2,8-bis(trifluoro-methyl)-quinoline-4-yl)-N-oxy-2-pyridyl-methane can also be prepared depending on the circumstances. This compound is novel. By using the suitable condensating agent or an excess of 2-methyl-pyridine-N-oxide depending on the solvent and/or by using a dilute reaction mixture substantially only mono-quinolyl-derivative is obtained.

According to process a. of the present invention one may preferably proceed by reacting a halogen-quinoline-derivative of the formula (III) with 2-methyl-pyridine-N-oxide in the presence of potassium tertiary-butylate using as the reaction medium tertiary alcohols or inert solvents, such as aromatic hyrocarbons, cyclic or acyclic ethers, dimethyl-formamide, dimethyl-sulphoxide preferably toluene or tetrahydrofuran.

According to the process variant b. one may preferably oxidize a compound of the formula (V) with per acids, preferably with peracetic acid or hydrogen-peroxide.

The starting material of process variant b. is the compound of the formula (V) or salts thereof which compounds are new. The compound of the formula (V) can be prepared from the derivatives of the formula (VI)

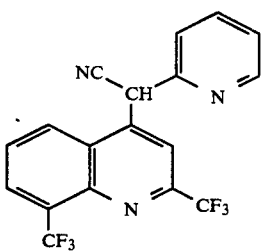

(VI)

or

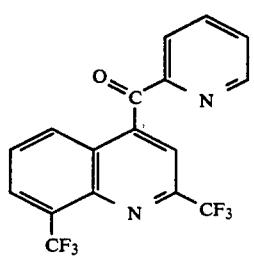

(VII)

by eliminating the nitrile or =O group.

The elimination of the nitrile group can be performed in an acid medium, such as sulphuric acid by heating in the presence of water.

The product can be obtained after neutralizing the reaction mixture by purification in a solvent in a crystalline form.

The elimination of the oxygen from the ketone derivative can be performed by catalytic reduction with hydrogen or transfer hydrogenolysis, preferably by a treatment with ammonium-formiate in the presence of a metal catalyst or formic acid.

The present invention also extends to the novel compounds of the formula (I), to the novel compound of the formula (V) and salts thereof.

The novel compounds according to the invention can be isolated from the reaction mixture as outlined in the following examples. If the compounds have to be converted to oxymethane by rearranging, then isolation from the reaction medium is not necessary, if the rearrangment is carried out by the method of our copending Hungarian patent application No. 3736/89 (see PCT/HU90/00049 corresponding to the concurrently filed U.S. application Ser. No. 671,917).

SPECIFIC EXAMPLES

The details of the present invention are shown in the following examples.

EXAMPLE 1

12.73 g of potassium-tert.-butylate and 6.20 g of 2-methyl-pyridine-N-oxide and 50 ml of tetrahydrofuran are mixed and to the mixture 3 g of 2,8-bis(trifluoro-methyl)-4-chloro-quinoline are added at 60° C. The mixture is allowed to cool to room temperature and 5 ml of glacial acetic acid is added dropwise under aqueous cooling to the mixture and the precipitated inorganic salt is filtered and washed with 2×20 ml ether. The organic layer is evaporated to dryness and the residual 9.31 g of product is admixed with an 1:1 mixture of ice and methanol, it is filtered, washed with water and dried. 3.42 g of N-oxy-2-pyridyl)-2,8-bis(trifluoro-methyl)-quinoline-4-methane are obtained. M.p.: 156°–158° C. An analytically pure sample is recrystalized twice from ethanol, m.p.: 162°–162.5° C.

EXAMPLE 2

16 g of potassium are dissolved in hot tertiary-butanol and the obtained potassium-tert.-butylate is suspended in 350 ml of toluene. To the suspension 21.8 g 2-methyl-pyridine-N-oxide and 24.1 g 2,8-bis(trifluoro-methyl)-4-bromo-quinoline are added at 45° C. The mixture is cooled to 20° C. and under external cooling 125 ml of 10% hydrochloric acid are added, the aqueous layer is separated and extracted with toluene. The organic layer is dried, clarified with active charcoal and evaporated to 150 g at reduced pressure. The mixture is cooled and the precipitated crystalline product is filtered. 20.12 g of (N-oxy-2-pyridyl)-2,8-bis(trifluoro-methyl)-quinoline-4-methane are obtained. Mp.: 157°–158° C.

EXAMPLE 3

To 100 ml of a 25% solution of potassium-tert.-pentylate in toluene 6 g of 2-methyl-pyridine-N-oxide and 3.44 g of 2,8-bis(trifluoro-methyl)-4-bromo-quinoline are added according to Example 1. 3.57 g of (N-oxi-2-pyridyl)-2,8-bis(trifluro-methyl)-quinoline-4-methane are obtained. M.p.: 155°–157° C.

EXAMPLE 4

To a solution prepared from 3.21 g of potassium metal and 80 ml of anhydrous tert.-butanol 4.4 g of 2-methyl-pyridine-N-oxide are added, the mixture is heated to 70° C. and 4.2 g of 2,8-bis(trifluoro-methyl)-4-chloroquinoline are added. When the reaction is terminated the pH is adjusted to 6 by adding concentrated hydrochloric acid solution, the mixture is stirred for 10 minutes at 25° C., the precipitated substance is filtered and covered with 10 ml of tert.-butanol. The mixture is concentrated by suction, dissolved in 100 ml of water and the insoluble part is filtered off and dried. 1.14 g of the product is obtained. Mp.: 264°-265° C. After recrystallization from methanol: Mp.: 271°-272° C. According to MS $^1$H- and $^{13}$C-NMR the product is di(2,8-bis(trifluoro-methyl)-4-quinolyl)-(N-oxy-2-pyridyl)-methane. From the aqueous tert-butanolic mother lye the tert.-butanol is distilled off and the residue is diluted with 100 ml of water, extracted with 3×50 ml chloroform, dried above sodium-sulphate and evaporated. After recrystallization of the residue 3.46 g of (N-oxy-2-pyridyl)-2,8-bis(trifluoro-methyl)-quinoline-4-methane are obtained. Mp.: 159°-161° C.

EXAMPLE 5

At 10° C. 350 ml of potassium-tert.-butylate are admixed in 2250 ml of hexane and 100 g of 2-methylpyridine-N-oxide are added. At this temperature the mixture is stirred for 1 hour, whereafter 100 g of 2,8-bis(trifluoro-methyl)-4-chloro-quinoline are added dropwise dissolved in 200 ml of hexane and after 6 hours of stirring at a temperature below 20° C. the mixture is neutralized by acetic acid. After 90 minutes the precipitated substance is filtered, washed with hexane, dried, admixed with 1000 ml of water and the insoluble raw product is filtered, washed with water and dried. 102.5 g of (N-oxy-2-pyridyl)-2,8-bis(trifluoro-methyl)-quinoline-4-methane are obtained. Mp.: 152°-154° C. Active ingredient content according to HPLC 83.2%.

EXAMPLE 6

To a mixture of 2250 ml of toluene and 250 g of potassium-tert-butylate of a temperature 0°-5° C. 70 g of freshly distilled 2-methyl-pyridine-N-oxide are added.

After stirring for 10 minutes 100 g of 2,8-bis(trifluoro-methyl)-4-chloro-quinoline are added dropwise in 150 ml of toluene within 60 minutes. After 90 minutes stirring the reaction mixture neutralized with glacial acetic acid is extracted with water. The residual toluene solution is clarified, filtered, evaporated and cooled. The precipitated crystalline product is filtered, covered with some toluene and dried. 89.9 g of (N-oxy-2-pyridyl)-2,8-bis(trifluoro-methyl)-quinoline-4-methane are obtained. Mp.: 157°-159° C. The product is of 95.6% purity according to HPLC.

EXAMPLE 7

125.0 g of potassium-tert.-butylate are dissolved in 2250 ml of abs. tetrahydrofuran, the mixture is cooled to 0°-5° C. and after adding 50.0 g of 2-methyl-pyridine-N-oxide 100 g of 2,8-bis(trifluoro-methyl)-4-chloro-quinoline dissolved in 150 ml of tetrahydrofuran are added dropwise. The solution is neutralized with acetic acid at a temperature below 20° C., the precipitated salt is filtered, and washed with tetrahydrofuran. The tetrahydrofuran solution is evaporated to a 1/10 volume and the precipitated product is filtered, washed with water and dried. 95.6 g of (N-oxy-2-pyridyl)-2,8-bis(trifluoro-methyl)-quinoline-4-methane are obtained.

M.p.: 159°-161° C.

The purity of the product according to HPLC=96.3%

EXAMPLE 8

1.0 g 2-pyridyl-2,8-bis(trifluoro-methyl)-quinoline-4-methane is dissolved in 10 ml of glacial acetic acid, and after adding 1.0 ml of 30% hydrogen peroxide the mixture is maintained at 80° C. for 90 minutes. The reaction mixture is poured on ice and extracted with chloroform. The organic layer is dried above sodium sulphate, evaporated and after recrystallization of the residue from 10 ml of ethanol 1 g of (N-oxy-2-pyridyl)-2,8-bis(trifluoro-methyl)-quinoline-4-methane is obtained.

EXAMPLE 9

10 g of 2-pyridyl-2,8-bis(trifluoro-methyl)-quinoline-4-acetonitrile are boiled under reflux for 5 hours in 70% sulfuric acid, the mixture is allowed to stand overnight, poured on ice and alkalized with concentrated ammonia to pH 9-10. The mixture is extracted with dichloroethane and the extract is dried above sodium sulphate and evaporated. The residue is crystallized from hexane and 6.47 of 2-pyridyl-2,8-bis(trifluoro-methyl)-quinoline-4-methane are obtained. Mp.: 62°-63° C.

EXAMPLE 10

Under vigorous stirring 5 g of 2-pyridyl-2,8-bis(trifluoro-methyl)-4-quinoline-ketone are maintained at 60° C. in 50 ml of 98% formic acid in the presence of 2 g of 10% Pd/C catalyst. In small portions 0.85 g of ammonium formiate are added. When the reaction is completed the catalyst is filtered off and the reaction mixture is evaporated. The residue is poured on ice and the mixture is worked up according to Example 9. 4 g of 2-pyridyl-2,8-bis(trifluoro-methyl)-quinoline-4-methane are obtained and the product melts after recrystallization from hexane at 57°-58° C.

We claim:

1. A process for the preparation of quinoline derivatives of the formula (I)

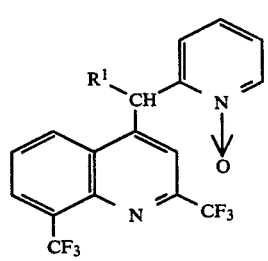

(I)

wherein

R$^1$ stands for hydrogen or a group of the formula (II)

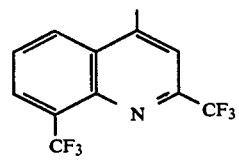

(II)

which comprises a.) reacting a halogen-quinoline-derivative of the formula (III)

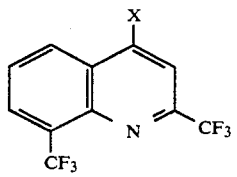

wherein X stands for chlorine or bromine
in the presence of alkalimetal-t-alkylate with α-picoline-N-oxide of the formula (IV)

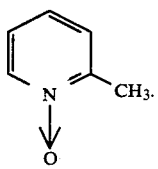

2. A process as claimed in claim 1 which comprises reacting a halogen-quinoline derivative of the formula (III), with α-picoline-N-oxide in the presence of potassium-tert.-butylate.

3. A compound of the formula (I)

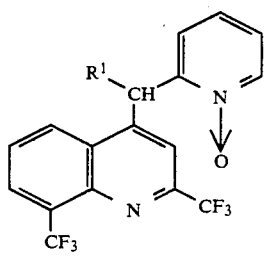

wherein R¹ stands for hydrogen or a group of the formula (II)

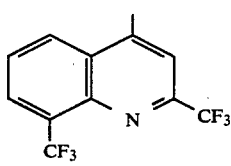

or a pharmaceutically acceptable salt thereof.

4. A process for the preparation of a compound of the Formula (I)

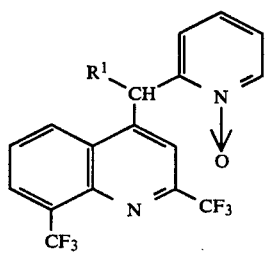

wherein

R¹ stands for hydrogen or a group of the Formula (II)

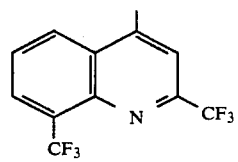

which comprises
reacting a compound of the Formula (III)

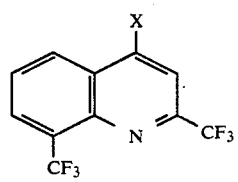

where X is chlorine or bromine, in the presence of an alkalimetal-t-alcoholate, with a compound of the Formula (IV)

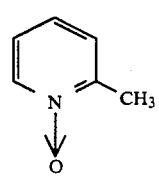

in a tertiary alcohol, aromatic hydrocarbon, cyclic or acyclic ether, dimethyl formamide or dimethyl sulfoxide as a reaction medium.

5. The process defined in claim 4 wherein the alkali-metal t-alcoholate is potassium t-butylate.

6. A process for the preparation of a compound of the Formula (I)

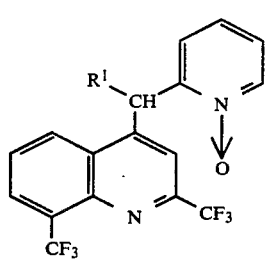

wherein
R¹ is hydrogen or a group of the Formula (II)

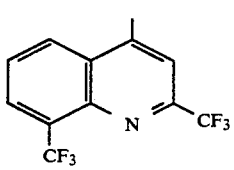

which comprises
N-oxidizing a compound of the Formula (V)

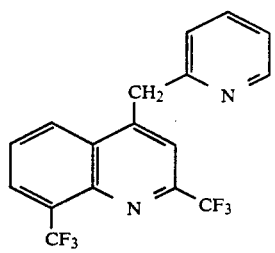 (V)
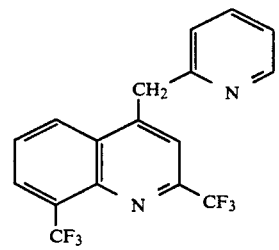 (V)
with peracetic acid or hydrogen peroxide.
with peracetic acid or hydrogen peroxide.
* * * * *